US011814597B2

(12) United States Patent
Deiana et al.

(10) Patent No.: US 11,814,597 B2
(45) Date of Patent: Nov. 14, 2023

(54) PROCESS FOR THE PRODUCTION OF OXIDIZED WOOD PRODUCTS

(71) Applicant: Organofuel Sweden AB, Sundsvall (SE)

(72) Inventors: Luca Deiana, Sundsvall (SE); Armando Cordova, Stockholm (SE); Ismail Ibrahem, Sundsvall (SE)

(73) Assignee: Organofuel Sweden AB, Sundsvall (SE)

( * ) Notice: Subject to any disclaimer, the term of this patent is extended or adjusted under 35 U.S.C. 154(b) by 0 days.

(21) Appl. No.: 17/426,862

(22) PCT Filed: Jan. 20, 2020

(86) PCT No.: PCT/EP2020/051277
§ 371 (c)(1),
(2) Date: Jul. 29, 2021

(87) PCT Pub. No.: WO2020/156857
PCT Pub. Date: Aug. 6, 2020

(65) Prior Publication Data
US 2022/0119722 A1     Apr. 21, 2022

(30) Foreign Application Priority Data

Jan. 31, 2019   (SE) .................................. 1950114-7
Mar. 20, 2019   (SE) .................................. 1950343-2

(51) Int. Cl.
*C10L 5/44*     (2006.01)
*C07C 45/38*    (2006.01)
(Continued)

(52) U.S. Cl.
CPC .............. *C10L 5/442* (2013.01); *C07C 45/38* (2013.01); *C07C 51/21* (2013.01); *C07G 1/00* (2013.01);
(Continued)

(58) Field of Classification Search
CPC .... C10L 5/442; C10L 9/06; C10L 5/36; C10L 2200/0469; C07C 45/38; C07C 51/21; C07G 1/00
See application file for complete search history.

(56) References Cited

U.S. PATENT DOCUMENTS 3,701,712 A * 10/1972 Samuelson et al. . D21C 9/1036
8/111
4,182,648 A *  1/1980 Pradt ..................... D21C 3/222
162/65

FOREIGN PATENT DOCUMENTS

AT        501929 B1    4/2007
CN     106400564 A    2/2017
(Continued)

OTHER PUBLICATIONS

International Search Report and Written Opinion in PCT/EP2020/051277 dated Apr. 20, 2020.
(Continued)

*Primary Examiner* — Cephia D Toomer
(74) *Attorney, Agent, or Firm* — Welsh IP Law LLC (57) ABSTRACT

The present invention relates to a process for the production of oxidized wood products, comprising step a) reacting chips of one or more wood products in a basic solution at a
(Continued)

Copper catalyzed oxidation of Lignin pH between 8 and 14 under an oxygen atmosphere at a pressure of at least 0.1 MPa, or at least 0.9 MPa. A copper catalyst may be used in the process.

12 Claims, 4 Drawing Sheets

(51) Int. Cl.
    *C07C 51/21*     (2006.01)
    *C07G 1/00*     (2011.01)
    *C10L 5/36*     (2006.01)
    *C10L 9/06*     (2006.01)

(52) U.S. Cl.
    CPC ............... *C10L 5/36* (2013.01); *C10L 9/06* (2013.01); *C10L 2200/0469* (2013.01)

(56) References Cited

FOREIGN PATENT DOCUMENTS

| | | |
|---|---|---|
| CN | 108164407 A | 6/2018 |
| CN | 108191619 A | 6/2018 |
| RU | 2059599 C1 | 5/1996 |
| RU | 2078755 C1 | 5/1997 |
| RU | 2119427 C | 9/1998 |
| RU | 2178405 C1 | 1/2002 |
| WO | 2000050621 A2 | 8/2000 |
| WO | 2013173316 A1 | 11/2013 |
| WO | 2014138707 A1 | 9/2014 |

OTHER PUBLICATIONS

European Paten Office Action in EP3891120A1 (related case) dated Jun. 30, 2022.
Indian Patent Office Action in related case dated Nov. 25, 2022.
Chinese Patent Office Action in related case dated Dec. 28, 2022.
Russian Office Search Report in Related Case (pp. 1-3) and English Translation by Google (p. 4-6) dated May 23, 2023.
Russian Office Action in Related Case (pp. 1-7) and English Translation (p. 8-12) dated May 23, 2023.
V.E. Tarabanko, Possibilities and Prospects for Creating a New Process for Processing Wood Into Products of Small-To-Nage Chemical Date unknown Technology Institute of Chemistry and Chemical Technology SB RAS, Krasnoyarsk, Russia.
X Z.Wang, J. Li Formation of Vanillin and Siringaldehyde in an Oxygen Delignnification Process, Bioresources, Aug. 2010, p. 1510-1515, table 1,2,3.
N.V. Tarabanko, M.A. Smirnova // Kinetics of Low-Temperature Oxidation of Enzymatic Pine Lignin (Pinus Silvestris) in Water-Alkaline Medium // Chemistry of Plant Raw Materials, 2017, pp. 66-67, fig. 1,3,4; table 2.
Chinese Office Action in related Case, including English Case by Agent dated Jul. 27, 2023.

\* cited by examiner

Fig. 1, Copper catalyzed oxidation of Lignin

FIG. 2A, GC – MS (EI) Analysis

- Peak 1: 2-Methoxyphenol
- Peak 2: Internal Standard
- Peak 3: Vanillin
- Peak 4: Acetovanillone
- Peak 5: Vanillic acid MS fragmentation of compounds Peak 1

Peak 3

FIG. 2B, GC – MS (EI) Analysis

FIG. 2C, GC – MS (EI) Analysis

PROCESS FOR THE PRODUCTION OF OXIDIZED WOOD PRODUCTS

FIELD OF THE INVENTION

The present invention relates to a process for the production of oxidized wood products, comprising step a) reacting chips of one or more wood products in a basic solution at a pH between 8 and 14 under an oxygen atmosphere at a pressure of at least 0.1 MPa, or at least 0.9 MPa. A copper catalyst may be used in the process.

BACKGROUND OF THE INVENTION

Wood products, such as short-rotation energy crops like lignin, softwoods and hardwoods, comprise alcohols that can be oxidized to produce among others vanillin, vanillic acid, acetovanillone, syringaldehyde, veratraldehyde and biofuels. It is a challenge to oxidize wood products at a large scale in an economically feasible manner. For large scale production, temperatures must be kept relatively low (i.e. below 200° C.) and the use of environmentally unfriendly solvents and catalysts is preferably prevented. For the oxidation of wood products, such as lignin, metal salts have been used. Sometimes the oxidations are done with catalysts, such as TEMPO. Copper salts and TEMPO may be used in combination. Solvents are almost always used.

For example, WO0050621 discloses the use of TEMPO with a copper histidine complex in an oxidation process. WO2014/138707 discloses the use of a solvent-free process for the oxidative depolymerisation of lignocellulosic material using a metal oxide layered in porphyrin-like material. These copper complexes are sensitive and expansive to use, which makes them unattractive to use for large scale processes.

AT501929 discloses a process, whereby primary alcohols are mixed with copper powder and a ligand, such as bipyridine in an organic solvent of water mixed with a nitrile, such as acetonitrile is used. Oxygen and TEMPO are added together with a base. No heterogenous complex molecules, such as those present in lignin, softwood or hardwood have been tested in this process. No enablement for temperatures under 100° C. is shown.

Liu K. et al, High-stable CuPd—$Cu_2O$/Ti-powder catalyst for low-temperature gas-phase selective oxidation of alcohols, Catalysis Comm 67, 54-58, 2015, discloses novel catalysts that can be used for oxidation of alcohols. The catalysts are copper-palladium or copper-titanium catalysts. The oxidation is performed at temperatures of 220° C. or more. No heterogenous complex molecules, such as those present in lignin, softwood or hardwood have been tested. In the introduction, the use of pure copper is discouraged.

Pande S. et al., Resin-immobilized CuO and Cu nanocompositions for alcohol oxidation, Org. Lett Vol 10, No 22, 5179-5181, 2008, discloses resin immobilized catalysts having a CuO-bound nanostructure. This application does not deal with oxidation of alcohols present in wood products. Further, the use of Cu bound nanostructure in contrast to CuO-bound nanostructure is discouraged several times in this article. No pure unbound copper has been tested, nor is there any information about temperatures used during an oxidation process.

The prior art discloses processes for oxidation of wood products in which either expensive catalysts are used, or costly and/or environmentally unfriendly solvents are used, or processes in which temperature or pressure are raised. All these process conditions prevent the processes from being used in a larger scale in an economically feasible manner.

Although much research has been done on lignin, there is little known about oxidation of wood itself, such as hardwood or soft food or lignin.

OBJECT AND SUMMARY OF THE INVENTION

It is an object of the present invention to at least partly overcome the above-mentioned problems, and to provide an improved process to produce oxidized wood products.

This object is achieved by a process for the production of oxidized wood products, comprising or consisting of step a) reacting chips of one or more wood products in a basic solution at a pH between 8 and 14 under an oxygen atmosphere at a pressure of at least 0.1 MPa. One aspect relates to the process for the production of vanillin, vanillic acid, acetovanillone, syringaldehyde, veratraldehyde and biofuels from wood products, such as soft and hardwoods.

An advantage of the new process is that the oxidation can be performed without using metal catalysts. This is especially advantageous for the production of chemicals from wood products that are to be used in pharmaceutical or food products. In one aspect, the use of a catalyst is disclaimed. In another aspect, the use of a metal catalyst is disclaimed.

In another aspect, the chips of the one or more wood products are unprepared and non-hydrolysed chips. In a further aspect, the wood product is raw cut chips of soft or hardwood or lignin, i.e. a wood product that has not been prepared chemically prior to entering the process of the invention. Another advantage of the process is that no chemical preparation, such as hydrolysis is needed prior to using the wood products in the process. This saves both time and costs. In an aspect, the one or more wood product has been mechanically prepared by cutting chips of the wood product. The chips may have an average diameter of about 2 cm, or between 0.1 and 10 cm.

In yet another aspect, the pressure is between 0.5 and 10 MPa, or at least 0.9 MPa. By increasing the pressure to between 0.8 and 2 MPa, the wood product oxidised quicker. In yet a further aspect, the pressure is between 0.9 and 1.1 MPa. Without wishing to be bound by any theories, an autocatalysis of the wood chips seems to be taken place at increased pressure. It is an advantage of the new process that oxidation of alcohols present in a wood product can be done on raw, untreated material by using oxygen and a base.

In another aspect, the pH in step a) is between 10 and 14, or between 12 and 14. By increasing the pH, the wood product(s) oxidised quicker.

In an aspect, the basic solution is an aqueous solution with bases selected from the group comprising or consisting of NaOH, KOH, $Ca(OH)_2$ and $Mg(OH)_2$. In one aspect, the base in the aqueous solution is NaOH. These bases are readily available at low costs, which minimized the costs for the overall process. These bases also allow for a scalability of the process.

In another aspect, the basic solution has a molarity of 5 M or less. Especially at pressures of at least 0.9 MPa, a relative low amount of 5 M or less can be used in the process compared to prior art processes. This lower amount of base improves process conditions, such as wear on equipment and safety. It reduces costs for the process. This also improves scalability of the process.

The invention relates to a process for the production of oxidized wood products, comprising or consisting of step a) reacting chips of one or more wood products in an aqueous solution with bases selected from the group comprising or consisting of NaOH, KOH, Ca(OH)$_2$ and Mg(OH)$_2$ having a molarity of 5 M or less and a pH between 8 and 14 under an oxygen atmosphere at a pressure of between 0.5 and 2 MPa, or at least 0.9 MPa. In another aspect, the pH is between 12 and 14. In a further aspect, the base is NaOH. In yet another aspect, substantially pure or pure oxygen is used. In yet a further aspect, the pressure is between 0.9 and 1.1 MPa.

Both air and oxygen may be used in the process of the invention. Advantageously, substantially pure or pure oxygen is used. The oxygen may have a purity of 95%, or 98% or 99%, or 99.9%. The purity of the oxygen improves the reaction rate of the oxidation process.

In one aspect, the use of air is disclaimed.

In an aspect, the temperature is below 160° C. The new process can be performed without using extreme temperature over 160° C., which reduces costs, especially when the process is performed at a large scale. In one aspect, the temperature is between 50 and 160° C., or between 60 and 150° C., or between 70 and 140° C., or between 71 and 110° C. The process of the invention, in which no catalysts is used, can be performed at relatively low temperatures compared to prior art processes. This improves safety and scalability of the process.

In another aspect, the one or more wood products are one or more short-rotation energy crops. A mixture of two or more species of short-rotation energy crops may be used in the process of the invention. In one aspect, one species of short-rotation energy crop is used. In a further aspect, the one or more wood products are one or more softwoods. In yet another aspect, the one or more softwoods are selected from the group comprising or consisting of pine, spruce, birch and cedar. In an aspect, the softwoods are selected from pine, spruce or birch, or a mixture thereof. In yet a further aspect, the one or more wood products are of one or more hardwoods. In one aspect, the one or more hardwoods are selected from the group comprising or consisting of aspen, beech, cotton woods, poplar, willow and *eucalyptus*. In an aspect, the hardwood is beech.

In an aspect, the one or more wood product is lignin. In another aspect, the one or more wood product is selected from the group comprising $C_{1-6}$alcohol, such as ethanol, hexanol or benzyl-$C_{1-6}$alcohol or oligomers of lignin or derivatives thereof.

The process of the invention can advantageously be used on different kinds of starting material, such as lignin, primary, secondary or tertiary alcohols and both softwoods and hardwoods. This improves the flexibility for the use of the process of the invention. The process allows for the production of vanillin, vanillic acid, acetovanilone, syringaldehyde, veratraldehyde and biofuels from different types of wood products. An advantage of this process is that no catalyst is needed for the oxidation. For the production of these compounds, only a base and oxygen, preferably substantially pure oxygen, are needed.

The invention relates to a process for the production of oxidized wood products, comprising or consisting of step a) reacting chips of one or more short-rotation energy crop in an aqueous solution with bases selected from the group comprising or consisting of NaOH, KOH, Ca(OH)$_2$ and Mg(OH)$_2$ having a molarity of 5 M or less and a pH between 8 and 14 under an oxygen atmosphere at a pressure of between 0.5 and 2 MPa, or at least 0.9 MPa at a temperature between 60 and 150° C. In one aspect, the short-rotation energy crop is lignin. In another aspect, the pH is between 12 and 14. In a further aspect, the base is NaOH. In yet another aspect, substantially pure or pure oxygen is used. In yet a further aspect, the pressure is between 0.9 and 1.1 MPa.

The invention also relates to a process for the production of oxidized wood products comprising or consisting of a step a) reacting the one or more wood product with oxygen gas or air in a water-based solvent comprising a liquid base at a pH between 8 and 14, whereby the process is performed under atmospheric pressure from 100500 to 102500 kPa, (i.e. about 0.1 MPa).

In one aspect, the base is selected from the group comprising or consisting of NaOH, KOH, Ca(OH)$_2$ and Mg(OH)$_2$.

The new process can be performed using any wood product, which means that waste products from any kind of plant material can be used. This reduces waste from wood products in general and allows this waste to be used to produce vanillin, vanillic acid, acetovanilone and the like. In one aspect, the wood product is selected from the groups comprising softwood, hardwood and lignin, or a mixture thereof. In another aspect, the wood product is selected from the groups comprising $C_{7-40}$alcohol, softwood, hardwood, polymers of lignin or derivatives thereof, paper, grass, plants, starches, grass, straw, herbaceous crops, saw dust, corn stover, other cellulose waste products and any combination thereof. In a further aspect, the temperature in step a) is between 60 and 150° C. In yet a further aspect, the temperature is between 71 and 110° C. In another aspect, a catalyst is added in step a), such as 2,2,6,6-tetramethylpiperidin-1-oxyl (TEMPO) or derivatives thereof, or 2-azaadamantane-N-oxyl.

In one aspect, step a) is performed under stirring for 6 to 36 hours.

In a further aspect, a Cu(0) catalyst in the form of pure copper is used in step a) and the pressure is below 0.7 MPa, or below 0.4 MPa, or below 0.2 MPa, or about 0.1 MPa, i.e. atmospheric pressure. By using a catalyst, the pressure can be reduced. This may reduce energy costs for the process. Copper may be used as pure copper in the form of a wire or a plate. The copper may be used as powder. In contrast to the teachings in the prior art, pure copper can be used in the process of the invention. This saves costs for using expensive complex-organocopper catalysts, which decreases the scalability of the process. It is an advantage of the new process that oxidation of alcohols present in a wood product can be done on raw, untreated material using oxygen and a base at temperatures below 160° C. In one aspect, Cu(0) catalyst is added to the process when the pressure in step a) is below 0.4 MPa, or below 0.2 MPa, or about 0.1 MPa.

In one aspect, the weight ratio of wood product to Cu(0) catalyst in step a) is from 50:1 to 1:1. The ratio may be 20:1 to 1:1.

The ratio in which the catalyst can be used to oxidize wood product is such that costs for the process are reduced. The ratio allows for simple scalability.

In one aspect, the process comprises a further step b) comprising neutralizing the oxidized product of step a) extracting the product with an organic phase and filtering the oxidized product. In an aspect, the temperature of the reaction mixture is reduced to room temperature prior to performing step b).

In a further aspect, the oxidized product is re-used in the process. Recycling of the oxidized product may increase the yield of the process and reduce the waste. Recycling can be done in an economically feasible manner because no environmentally unfriendly solvents are used in the process.

In another aspect, the Cu(0) catalyst is reused.

In one aspect, step a) is performed under stirring for 6 to 36 hours.

Recycling of the catalyst reduces costs for the process and improves the environmentally friendliness of the process.

In an aspect, the invention relates to a process for the production of oxidized wood products, comprising or consisting of step a1) reacting chips of one or more wood products with a Cu(0) catalyst and oxygen gas or air in an non-aqueous organic solvent at a pressure of about 0.1 MPa.

Optionally the process comprises or consist of a step a2) adding an aqueous basic solution at a pH between 8 and 14.

The invention thus relates to a process for the production of oxidized wood products, comprising a step a1) reacting the one or more wood product with a Cu(0) catalyst and oxygen gas or air in a non-aqueous and solvent-free environment (water or an organic solvent) under atmospheric pressure from 100500 to 102500 kPa (about 0.1 MPa).

With the new process, $C_{1-6}$alcohol, such as ethanol, hexanol or benzyl-$C_{1-6}$alcohol or oligomers of lignin or derivatives thereof, can be oxidized without using an organic solvent. The process can be performed at atmospheric pressure. The process can thus be performed at reduced costs. Also, the new process is more environmentally friendly compared to known processes because less energy is needed to perform the process (i.e. lower pressure compared to the prior art processes) and no aggressive chemicals are needed as solvents. The new process is scalable, which is important, for example for production of biofuels and handling waste from paper industries. The catalyst used may be a copper wire or copper plate, or pieces thereof, or copper powder. No complex organo-copper catalysts are needed. This further reduces costs and improves scalability of the process. The process may be used to produce vanillin, vanillic acid, acetovanilone, syringealdehyde, veratraldehyde and biofuels.

Both air and oxygen may be used in step a1). In another aspect, oxygen is used. In a further aspect, air is used. Advantageously, substantially pure or pure oxygen is used. The oxygen may have a purity of 95%, or 98% or 99%, or 99.9%. The purity of the oxygen improves the reaction rate of the oxidation process.

In an aspect, the temperature in step a1) is below 160° C. In one aspect, the temperature is between 50 and 160° C., or between 60 and 150° C., or between 70 and 140° C., or between 70 and 110° C. The process, in which no catalysts is used, can be performed at relatively low temperatures compared to prior art processes. The reduces costs and improves safety and scalability of the process.

In a further aspect, the base in step a2) is selected from the groups comprising or consisting of NaOH, KOH, Ca(OH)$_2$ and Mg(OH)$_2$. In one aspect, the base is NaOH. In another aspect, toluene may be added as a solvent.

The molarity of the basic solution in step a2) may be 5 M or less, or below 4 M or less, or between 3 and 5 M. The pH may be between 10 and 14, or between 12 and 14.

Different readily available bases can be used, which are obtainable at low costs. Water can be used as a solvent in the process, which is more environmentally friendly and cheaper compared to the solvents used in the prior art processes. This reduces costs for the overall process and improves the environmentally friendliness of the process as well as scalability.

In one aspect, step a1) is performed under stirring for 6 to 36 hours.

In another aspect, the one or more wood products are one or more short-rotation energy crops. A mixture of two or more species of short-rotation energy crops may be used in the process of the invention. In one aspect, one species of short-rotation energy crop is used. In a further aspect, the one or more wood products are one or more softwoods. In yet another aspect, the one or more softwoods are selected from the group comprising or consisting of pine, spruce, birch and cedar. In an aspect, the softwoods are selected from pine, spruce or birch, or a mixture thereof. In yet a further aspect, the one or more wood products are of one or more hardwoods. In one aspect, the one or more hardwoods are selected from the group comprising or consisting of aspen, beech, cotton woods, poplar, willow and *eucalyptus*. In an aspect, the hardwood is beech.

In an aspect, the one or more wood product is lignin. In another aspect, the one or more wood product is selected from the group comprising $C_{1-6}$alcohol, such as ethanol, hexanol or benzyl-$C_{1-6}$alcohol or oligomers of lignin or derivatives thereof.

The process of the invention can advantageously be used on different kinds of starting material, such as lignin, primary, secondary or tertiary alcohols and both softwoods and hardwoods. This improves the flexibility for the use of the process of the invention.

In one aspect, the wood product is selected from the groups comprising or consisting of $C_{1-6}$alcohol, such as ethanol, hexanol or benzyl-$C_{1-6}$alcohol or oligomers of lignin or derivatives thereof. In yet another aspect, the process is performed on both primary and secondary alcohols. In yet a further aspect, the process is performed on secondary alcohols only. In another aspect, the process is performed on primary alcohols only. In yet another aspect, the process is performed on straight or branched $C_{1-6}$-alkohols. In one aspect, the wood product is ethyl alcohol, hexanol or benzyl alcohol.

In one aspect, the wood product is selected from the groups comprising or consisting of $C_{7-40}$alcohol, softwood, hardwood, polymers of lignin or derivatives thereof, paper, grass, plants, starches, grass, straw, herbaceous crops, saw dust, corn stover, other cellulose waste products and any combination thereof. The process can be performed using raw materials, such as wood and plants. The raw material does not need to be prepared or processed prior to use in the process of the invention. This reduces costs and improves efficiency of removal waste wood products.

In one aspect, the process steps a), a1), a2) and b) are performed free of ligands. In one aspect, the process of the invention is performed free of nitrile. In another aspect, the process is performed free of co-catalysts. Co-catalyst, such as TEMPO are expensive and may be toxic. Such co-catalysts must be recycles/recovered after the process to prevent damages to the environment. Not having to use a co-catalyst thus reduces costs as well as the impact of the process on the environment.

In a further aspect, the process is performed in a one-pot.

In one aspect, the weight ratio of wood product to Cu(0) catalyst steps a1) is from 50:1 to 1:1. The ratio may be 20:1 to 1:1.

The ratio in which the catalyst can be used to oxidize wood product is such that costs for the process are reduced. The ratio allows for simple scalability.

In another aspect, a co-catalyst is added in step a) or a1), such as 2,2,6,6-tetramethylpiperidin-1-oxyl (TEMPO) or derivatives thereof, or 2-azaadamantane-N-oxyl.

The co-catalyst is readily available. The co-catalyst can be used when the process is used on a large industrial scale. The ratio of catalyst to co-catalyst may be from 20:1 to 1:1, or from 1:2 to 1:1. The ratio of co-catalyst to wood product may be from 1:40 to 1:20, or from 1:10 to 1:20. The ratio of wood product to catalyst to co-catalyst may be from 50:1:1 to 50:1:2 to 20:20:1, or from 20:1:1 to 20:1:2 to 20:20:1.

The ratio can be used to oxidize wood product is such that costs for the process are reduced. The ratio allows for simple scalability.

In one aspect, the process comprises a further step b) comprising neutralizing the oxidized product of step a1), a2), extracting the product with an organic phase and filtering the oxidized product. In an aspect, the temperature of the reaction mixture is reduced to room temperature prior to performing step b).

The final cleaning of the oxidized products can be done in a well-known manner using cheap and readily available material. The base used in step a2) can easily be neutralized to prevent any impact of the base on the environment.

In one aspect, the oxidized product is re-used in the process.

In another aspect, the Cu(0) catalyst is reused.

Recycling of the catalyst reduces costs for the process and improves the environmentally friendliness of the process.

BRIEF DESCRIPTION OF THE DRAWINGS

The invention will now be explained more closely by the description of different embodiments of the invention and with reference to the appended figures.

DETAILED DESCRIPTION OF PREFERRED EMBODIMENTS OF THE INVENTION

As used herein "short-rotation energy crops" means fast growing softwoods, such as pine, spruce, birch and cedar or hardwoods, such as aspen, cotton woods, poplar, willow and *eucalyptus*.

Wt % as used herein are percentages of the total weight of the solution or of the final material.

The invention relates to a process for the production of oxidized wood products, comprising or consisting of step a) reacting chips of one or more wood products in a basic solution at a pH between 8 and 14 and under an oxygen atmosphere at a pressure of at least 0.1 MPa. The process of the invention may be used for the production of vanillin, vanillic acid, acetovanillone, syringaldehyde, veratraldehyde and biofuels from wood products, such as soft and hardwoods, lignin. The process is especially useful for the production of compounds that can be used in pharmaceutical or cosmetic products or in food products.

The chips of the wood product used in the process do not need to be prepared prior to use in the process. Thus, no hydrolysis or washing of the chips is needed. The wood product may be mechanically prepared by cutting the wood product into chips. The chips may have an average diameter of about 0.2 cm, or between, 0.1 and 10 cm.

The process may be performed at a pressure of at least 0.7 or 0.9 MPa. By increasing the pressure to between 0.8 and 2 MPa, the wood product oxidises quicker. The pressure may be between 0.5 and 10 MPa, or between 0.5 and 2 MPa, or between 0.5 and 1.5 MPa, or between 0.9 and 1.1 MPa or about 1.0 MPa.

The basic solution is an aqueous solution with bases selected from the group comprising or consisting of NaOH, KOH, Ca(OH)$_2$ and Mg(OH)$_2$. The base may be NaOH.

The basic solution has a molarity of 5 M or less. The basic solution may have a molarity 4.5 M or less, or 4 M or less, or 3.5 M or less. The basic solution may be a 3 to 5 M, or 4 M NaOH aqueous solution.

Both air and oxygen may be used in the process of the invention. Advantageously, substantially pure or pure oxygen is used. The oxygen may have a purity of 95%, or 98% or 99%, or 99.9%.

The invention relates to a process for the production of oxidized wood products, comprising or consisting of step a) reacting chips of one or more wood products in an aqueous solution with NaOH as a base having a molarity of 5 M or less and a pH between 12 and 14 under an oxygen atmosphere at a pressure between 0.9 and 1.1 MPa. Substantially pure or pure oxygen may be used.

The temperature used in step a) is below 160° C., or 50 and 160° C., or between 60 and 150° C., or between 70 and 140° C., or between 71 and 139° C. or between 71 and 109° C. The reaction time for step a) depends on the temperature. An optimum reaction time can be achieved when the process is performed at a temperature between 71 and 139° C.

The wood products are one or more short-rotation energy crops. A mixture of two or more species of short-rotation energy crops may be used in the process of the invention, Commonly, one species of short-rotation energy crop is used. The one or more wood products may be one or more softwoods. The one or more softwoods may be selected from the group comprising or consisting of pine, spruce, birch and cedar, or mixtures thereof. The wood product may be one or more hardwoods. The one or more hardwoods may be selected from the group comprising or consisting of aspen, cotton woods, poplar, beech, willow and *eucalyptus*, or mixtures thereof.

The wood product may be lignin or oligomers of lignin or derivatives thereof. The process of the invention may also be used for oxidation of substantial pure primary, secondary and/or tertiary alcohols, in which case the wood product may be selected from the group comprising $C_{1-6}$alcohol, such as ethanol, hexanol or benzyl-$C_{1-6}$alcohol, or mixtures thereof. The invention relates to a process for the production of oxidized wood products, comprising or consisting of step a) reacting chips of one or more softwood in an aqueous solution with NaOH as a base NaOH having a molarity of 3 to 5 M and a pH between 12 and 14 under an oxygen atmosphere at a pressure between 0.9 and 1.1 MPa at a temperature between 60 and 150° C. The softwood may be lignin. Substantially pure or pure oxygen may be used.

The process may be performed at atmospheric pressure of about 0.1 MPa. The process for the production of oxidized wood products may then comprise or consist of a step a) reacting the one or more wood product with oxygen gas or air in a water-based solvent comprising a liquid base at a pH between 8 and 14, whereby the process is performed under atmospheric pressure from 100500 to 102500 kPa, (i.e. about 0.1 MPa).

The base may be selected from NaOH, KOH, Ca(OH)$_2$ and Mg(OH)$_2$. The molarity of the basic aqueous solution may be between 2 and 6 M, or between 3 and 5 M.

The wood product may be as defined anywhere herein. In the process performed at atmospheric pressure of about 0.1 MPa, suitable the wood product may be selected from the groups comprising or consisting of $C_{7-40}$alcohol, softwood, hardwood, polymers of lignin or derivatives thereof, paper, grass, plants, starches, grass, straw, herbaceous crops, saw dust, corn stover, other cellulose waste products and any combination thereof.

The temperature of the process performed at atmospheric pressure of about 0.1 MPa may be between 60 and 150° C. or between 71 and 110° C.

In one aspect, a Cu(0) catalyst in the form of pure copper may be used in step a) when the pressure is below 0.9 or 0.7, or 0.4, or 0.2 MPa or at atmospheric pressure (0.1 MPa). Copper may be used as pure copper in the form of pieces of a wire or a plate. The weight ratio of wood product to Cu(0) catalyst is from 50:1 to 1:1. The ratio may be 20:1 to 1:1 or 20:1 to 2:1. The ratio may be 50:1 to 5:1.

In another aspect, the Cu(0) catalyst is reused.

A (co-)catalyst may be added in step a). Examples of a non-metal (co-)catalyst may be 2,2,6,6-tetramethylpiperidin-1-oxyl (TEMPO) or derivatives thereof, or 2-azaadamantane-N-oxyl.

Any kind of short-rotation energy crop as defined herein may be used in this process. In the process performed at atmospheric pressure of about 0.1 MPa, and using a none metal catalyst, suitable wood products may be selected from the groups comprising softwood, hardwood, lignin, paper, grass, plants, starches, grass, straw, herbaceous crops, saw dust, corn stover, other cellulose waste products and any combination thereof.

Oxygen or air may be used in the process using the non-metal catalyst, or substantially pure oxygen may be used. The amount of non-metal (co-)catalyst used may be from 1 to 10 mol %, or from 2 to 7 mol %, or about 5 mol %.

In one aspect, step a) is performed under stirring for 6 to 36 hours.

The process may also comprise or consist of step a1) of reacting the wood product with a Cu(0) catalyst and oxygen gas or air in a non-aqueous and solvent-free environment (i.e. water or organic solvent) under atmospheric pressure and optionally adding a co-catalyst, and step a2) adding a liquid base at a pH between 8 and 14 in a water-based solvent, under atmospheric pressure (about 0.1 MPa).

The Cu(0) catalyst may be a copper wire or plate, or pieces thereof, or copper powder. The reaction mixture may be heated to a temperature from 50 to 150° C., or from 75 to 105° C. The reaction is preferably performed under stirring for between 4 and 48 hours, or between 12 and 36 hours or between 6 and 36 hours.

The base may be selected from NaOH, KOH, $Ca(OH)_2$ and $Mg(OH)_2$. One base may be NaOH. The base may be used at a concentration of 1 to 5 M, or about 2 M.

Examples of a co-catalyst are 2,2,6,6-tetramethylpiperidin-1-oxyl (TEMPO) or derivatives thereof, or 2-azaadamantane-N-oxyl.

The amount of co-catalyst used may be from 1 to 10 mol %, or from 2 to 7 mol %, or about 5 mol %.

The ratio of catalyst to co-catalyst may be from 20:1 to 1:1, or from 1:2 to 1:1.

The ratio of co-catalyst to wood product may be from 1:100 to 1:20, or from 1:14 to 1:20.

The ratio of wood-product to catalyst to co-catalyst may be from 50:1:1 to 50:1:2 to 20:20:1, or from 20:1:1 to 20:1:2 to 20:20:1.

The process may comprise a further step b) comprising neutralizing the oxidized product of step a), extracting the product with an organic phase and filtering the oxidized product. Prior to performing step b), the temperature of the reaction mixture may be reduced to room temperature.

Preferably, the reaction mixture obtained after step a) is cooled down to room temperature prior to performing step b). Neutralization may be done by adding an acid to the reaction mixture, such a hydrochloride (HCl) or sulfuric acid, and the like. The pH of the neutralized solution may be below 7, such as between 1 and 5, or about 2.

The aqueous phase obtained after filtering and neutralization may be extracted with an organic solvent. Examples of organic solvents may be ethyl acetate (EtOAc), diethyl ether ($Et_2O$) and dichloromethane ($CH_2Cl_2$). The extracted organic phase can be evaporated, and the crude mixture filtered through e.g. a short silica gel column.

Process step b) is performed at atmospheric pressure from 100500 to 102500 kPa, or 101325 kPa (about 0.1 MPa).

The solid material obtained after filtering may be reused in the process. The solid material may be filtered off and washed with water and then reused in the next cycle of the process.

The Cu(0) catalyst may also be reused or recycled. After filtering, the Cu(0) catalyst can be cleaned by washing the catalyst with an acid, e.g. 2M HCl. A black layer formed on the catalyst may be scraped off, after which the catalyst can be washed with water before reusing the catalyst in the next process.

The invention thus relates to a process for oxidation of alcohols, which process may be performed as outlined below.

I-a) The process may comprise or consist of step a) reacting chips of one or more wood products in a basic solution at a pH between 10 and 14 under an oxygen atmosphere at a pressure of at least 0.9 MPa, and step b) of neutralizing the oxidized product of step a), extracting the product with an organic phase and filtering the oxidized product.

I-b) The process may comprise or consist of step a) of reacting the wood products with oxygen gas or air in a water-based solvent comprising a liquid base at a pH between 8 and 14, whereby the process is performed under atmospheric pressure from 100500 to 102500 kPa (about 0.1 MPa), and step b) of neutralizing the oxidized product of step a), extracting the product with an organic phase and filtering the oxidized product.

I-c) The process may comprise or consist of step a) reacting chips of one or more wood products in a basic solution at a pH between 10 and 14 under an oxygen atmosphere at a pressure of at 0.7 MPa or less, in the presence of a Cu(0) catalyst, and step b) of neutralizing the oxidized product of step a), extracting the product with an organic phase and filtering the oxidized product.

I-d) The process may comprise or consist of step a) reacting chips of one or more wood products in a basic solution at a pH between 10 and 14 under an oxygen atmosphere at a pressure of at 0.7 MPa or less, in the presence of a non-metal catalyst, such as TEMPO, and step b) of neutralizing the oxidized product of step a), extracting the product with an organic phase and filtering the oxidized product.

The one or more wood products in processes I-a to I-d may be selected from the groups comprising or consisting of $C_{7-40}$alcohol, softwood, hardwood, polymers of lignin or derivatives thereof, paper, grass, plants, starches, grass, straw, herbaceous crops, saw dust, corn stover, other cellulose waste products and any combination thereof.

The one or more wood products may be one or more softwoods. The one or more softwoods may be selected from the group comprising or consisting of pine, spruce, birch and cedar, or mixtures thereof. The wood product may be one or more hardwoods. The one or more hardwoods may be selected from the group comprising or consisting of aspen, cotton woods, poplar, beech, willow and *eucalyptus*, or mixtures thereof.

The wood product may be lignin or oligomers of lignin or derivatives thereof. The process of the invention may also be used for oxidation of substantial pure primary, secondary and/or tertiary alcohols, in which case the wood product may be selected from the group comprising $C_{1-6}$alcohol, such as ethanol, hexanol or benzyl-$C_{1-6}$alcohol, or mixtures thereof.

II-a1) The process may comprise or consist of
- step a1) of reacting the wood product with a Cu(0) catalyst and oxygen gas or air in a non-aqueous and solvent-free environment (i.e. water or organic solvent) at atmospheric pressure (about 0.1 MPa), and
- step b) of neutralizing the oxidized product of step a1), extracting the product with an organic phase and filtering the oxidized product.

II-b) The process may comprise or consist of
- step a1) of reacting the wood product with a Cu(0) catalyst and oxygen gas or air in a non-aqueous and solvent-free environment (i.e. water or organic solvent), and a co-catalyst, such as TEMPO, and
- step b) of neutralizing the oxidized product of step a1), extracting the product with an organic phase and filtering the oxidized product,
- whereby the process is performed under atmospheric pressure from 100500 to 102500 kPa (about 0.1 MPa).

The wood product in processes II-a or II-b may be selected from the groups comprising or consisting of $C_{1-6}$alcohol, such as ethanol, hexanol or benzyl-$C_{1-6}$alcohol or oligomers of lignin or derivatives thereof. The process may be performed on straight or branched $C_{1-6}$alcohols, such as primary and/or secondary alcohols. Examples of such alcohols may be methanol, ethyl alcohol, such as ethanol, propyl alcohol, such as isopropanol, butyl alcohol, such a 1-butanol, pentyl alcohol, such as 1-pentanol or hexyl alcohol, such as 1-hexanol. The alcohol may be ethyl alcohol or hexanol. The alcohol may be benzyl-alcohol, such as phenyl methanol. The one or more wood products may be one or more softwoods. The one or more softwoods may be selected from the group comprising or consisting of pine, spruce, birch and cedar, or mixtures thereof. The wood product may be one or more hardwoods. The one or more hardwoods may be selected from the group comprising or consisting of aspen, cotton woods, poplar, beech, willow and *eucalyptus*, or mixtures thereof.

The wood product may be lignin or oligomers of lignin or derivatives thereof. The process of the invention may also be used for oxidation of substantial pure primary, secondary and/or tertiary alcohols, in which case the wood product may be selected from the group comprising $C_{1-6}$alcohol, such as ethanol, hexanol or benzyl-$C_{1-6}$alcohol, or mixtures thereof.

III-a) The process may comprise or consist of
- step a1) of reacting the wood product with a Cu(0) catalyst and oxygen gas or air in a non-aqueous and solvent-free environment (i.e. water or organic solvent), and
- step a2) adding a liquid base at a pH between 8 and 14 in a water-based solvent, and
- step b) of neutralizing the oxidized product of step a2), extracting the product with an organic phase and filtering the oxidized product,
- whereby the process is performed under atmospheric pressure from 100500 to 102500 kPa (about 0.1 MPa).

III-b) The process may comprise or consist of
- step a1) of reacting the wood product with a Cu(0) catalyst and oxygen gas or air in a non-aqueous and solvent-free environment (i.e. water or organic solvent), and a co-catalyst, such as TEMPO, and
- step a2) adding a liquid base at a pH between 8 and 14 in a water-based solvent, and
- step b) of neutralizing the oxidized product of step a2), extracting the product with an organic phase and filtering the oxidized product,
- whereby the process is performed under atmospheric pressure from 100500 to 102500 kPa (about 0.1 MPa).

The wood product in processes III-a or III-b may be selected from the groups comprising or consisting of $C_{7-40}$alcohol, softwood, hardwood, polymers of lignin or derivatives thereof, paper, grass, plants, starches, grass, straw, herbaceous crops, saw dust, corn stover, other cellulose waste products and any combination thereof. The one or more wood products may be one or more softwoods. The one or more softwoods may be selected from the group comprising or consisting of pine, spruce, birch and cedar, or mixtures thereof. The wood product may be one or more hardwoods. The one or more hardwoods may be selected from the group comprising or consisting of aspen, cotton woods, poplar, beech, willow and *eucalyptus*, or mixtures thereof.

The wood product may be lignin or oligomers of lignin or derivatives thereof. The process of the invention may also be used for oxidation of substantial pure primary, secondary and/or tertiary alcohols, in which case the wood product may be selected from the group comprising $C_{1-6}$alcohol, such as ethanol, hexanol or benzyl-$C_{1-6}$alcohol, or mixtures thereof. The solid material obtained after filtering may be reused in the process. The solid material may be filtered off and washed with water and then reused in the next cycle of the process.

The Cu(0) catalyst may also be reused or recycled. After filtering, the Cu(0) catalyst can be cleaned by washing the catalyst with an acid, e.g. 2M HCl. A black layer formed on the catalyst may be scraped off, where after the catalyst can be washed with water before reusing the catalyst in the next process.

The obtained oxidized product may comprise vanillin, vanillic acid, acetovanillone, syringaldehyde, veratraldehyde and biofuels, or mixtures thereof.

EXAMPLES

Wt % is defined as a percentage of the total weight of the wood product as start material.

Example 1

Oxidation of Soft and Hardwood

To a 1.0-liter metal reaction vessel (laboratory digester), was charged with chips of either softwood (mixture of spruce and pine) or hardwood (e.g. beech), 24 g, 1.0 equiv.) and 200-600 mL NaOH 2-5 M. The laboratory digester was sealed, and the atmosphere changed to oxygen (0.5-1 MPa of $O_2$ was applied). Next, the resulting mixture was allowed to blend at 70-140° C. for 8-18 h in a laboratory rotary digester.

Then, the reaction temperature was decreased to room temperature. Next, the residue unreacted wood was filtered, and the reaction mixture acidified to pH=2, with 12 M HCl by slow addition of HCl. Next, the aqueous phase was extracted with an organic solvent (EtOAc). The extracted organic phase was evaporated, and the crude mixture was filtered through short silica gel column.

For softwood (table 1, Entry 4), the synthesis produced 10.4 wt % vanillin, 2.2 wt % acetovanillone and 6.3 wt % vanillic acid. The calculations are based on the GC-MS analysis and confirmed by H-NMR analysis of the isolated product. See table 1.

For hardwood (table 2), the synthesis produced 3.83 wt % vanillin, 0.98 wt % acetovanilone, 3.88 wt % vanillic acid, 4.05 wt % syringaldehyde, 0.58 wt % acetosyringone and 2.68 wt % syringic acid. The calculations are based on the GC-MS analysis and confirmed by H-NMR analysis of the isolated product. See table 2. Wt % are percentages of the total weight of the isolated product obtained after chromatography through the silica gel in respective to amount of lignin or wood chip.

TABLE 1

Oxidation of softwood

| Entry[a] | NaOH [M] | Temp. [° C.] | Time [h] | a Wt [%][b] | b Wt [%][b] | c Wt [%][b] | d Wt [%][b] |
|---|---|---|---|---|---|---|---|
| 1 | 2.0 | 100 | 6.5 | 1.87 | 0.14 | 1.02 | — |
| 2 | 2.0 | 130 | 6.5 | 7.46 | 0.93 | 0.96 | — |
| 3 | 4.0 | 130 | 6.5 | 9.06 | 2.08 | 1.93 | — |
| 4 | 4.0 | 130 | 13.0 | 10.4 | 2.2 | 6.3 | — |

[a]24 g, 122 mmol of soft wood were used here. Concentration, C = 0.3 M, under 10 bar $O_2$.
[b]Calculated yields based on GC-mass.
10 bar = 1 MPa

TABLE 2

Oxidation of hardwood

TABLE 2-continued e          f

| Entry[a] | NaOH [M] | Temp. [° C.] | Time [h] | a Wt [%][b] | b Wt [%][b] | c Wt [%][b] | d Wt [%][b] | e Wt [%][b] | f Wt [%][b] |
|---|---|---|---|---|---|---|---|---|---|
| 1 | 2.0 | 100 | 6.5 | 3.84 | 0.98 | 3.88 | 4.06 | 0.58 | 2.68 |

[a]24 g, 122 mmol of soft wood were used here. Concentration, C = 0.3 M, under 10 bar $O_2$.
[b]Calculated yields based on GC-mass (hard wood lignin content is 22.4%).
10 bar = 1 MPa

Example 2

Large Scale Production of Oxidation of Soft and Hardwood
100 Liter Scale

To a 100-liter metal reaction reactor (digester) is charged with wood (soft or hard, 10 kg, 1.0 equiv.) and 50 l NaOH 2-5 M. The reactor (digester) is then sealed and the atmosphere changed to oxygen (0.5-1 MPa of $O_2$ is applied). Next, the resulting mixture is allowed to blend at 70-140° C. for 8-18 h.

Then, the reaction temperature is decreased to room temperature. The residue of unreacted wood is filtered, and the reaction mixture is acidified to pH=2, with 12 M HCl by slowly adding HCl. Next, the aqueous phase is extracted with an organic solvent. The extracted organic phase is evaporated, distilled and re-used/recycled and vanillin is purified by recrystallization.

1000 Liter Scale

To a 1000-liter metal reaction reactor (digester) is charged with wood (soft or hard, 100 kg, 1.0 equiv.) and 500 l NaOH 2-5 M. The reactor (digester) is then sealed and the atmosphere changed to oxygen (0.5-1 MPa of $O_2$ was applied). Next, the resulting mixture is allowed to blend at 70-140° C. for 8-18 h.

Then, the reaction temperature is decreased to room temperature. The residue of unreacted wood is filtered, and the reaction mixture is acidified to pH=2, with 12 M HCl by slowly adding HCl. Next, the aqueous phase is extracted with an organic solvent. The extracted organic phase is evaporated, distilled and re-used/recycled and vanillin is purified by recrystallization.

Example 3

Procedure for the Cu(0)-Plate Catalyzed Catalytic Aerobic Oxidation Under Solvent-Free Conditions at Atmospheric Pressure.

Ethyl Alcohol

An oven-dried microwave vial (8 ml) equipped with a magnetic stir bar was charged with Cu(0)-plate (200-250 mg, 3×4 cm surface) and TEMPO (20 mg, 5 mol %). The vial was then sealed and ethyl alcohol (117 μl, 2 mmol) was added. The atmosphere was changed to oxygen and an oxygen balloon was connected to the reaction vessel. The resulting mixture was allowed to stir at 70° C. for 16 h. The reaction mixture was then diluted with $CHCl_3$, and the formation of the corresponding acetaldehyde was confirmed by H-NMR.

Benzyl Alcohol

An oven-dried microwave vial (8 mL) equipped with a magnetic stir bar was charged with Cu(0)-wire (26 mg, 30 wt %, the Cu(0)-wire were cut into small pieces) and TEMPO (7 mg, 5 mol %). The vial was sealed, and the atmosphere was changed to oxygen and an oxygen balloon was connected to the reaction vessel. Next, benzyl alcohol (83 μl, 0.8 mmol) was added and the resulting mixture was allowed to stir at 70° C. for 16 h. The reaction mixture was diluted with $CHCl_3$ and the formation of the corresponding acetaldehyde was confirmed by H-NMR.

Hexanol

An oven-dried microwave vial (8 ml) equipped with a magnetic stir bar was charged with Cu(0)-wire (24 mg, 30 wt %, the Cu(0)-wire cut into small pieces) and TEMPO (7 mg, 5 mol %). The vial was then sealed, the atmosphere was changed to oxygen and an oxygen balloon was connected to the reaction vessel. Next, hexanol (100 μl, 0.8 mmol) was added. The resulting mixture was allowed to stir at 100° C. for 16 h. The reaction mixture was diluted with $CHCl_3$ and the formation of the corresponding hexanal was confirmed by H-NMR.

Ethyl Alcohol

An oven-dried microwave vial (8 ml) equipped with a magnetic stir bar was charged with Cu(0)-wire (11 mg, 30 wt %, the Cu(0)-wire were cut into small pieces) and TEMPO (7 mg, 5 mol %). The vial was sealed, and the atmosphere was changed to oxygen and an oxygen balloon was connected to the reaction vessel. Next, ethyl alcohol (47 μl, 0.8 mmol) was added and the resulting mixture was allowed to stir at 70° C. for 16 h. The reaction mixture was diluted with $CHCl_3$ and the formation of the corresponding acetaldehyde was confirmed by H-NMR.

Hexanol

An oven-dried microwave vial (8 ml) equipped with a magnetic stir bar was charged with Cu(0)-wire (24 mg, 30 wt %, the Cu(0)-wire were cut into small pieces) and TEMPO (7 mg, 5 mol %). The vial was sealed, and the atmosphere changed to oxygen and an oxygen balloon was connected to the reaction vessel. Next, toluene (2.0 ml, C=0.4 M) and hexanol (100 μl, 0.8 mmol) was added. The resulting mixture was allowed to stir at 100° C. for 16 h. The reaction mixture was diluted with $CHCl_3$ and the formation of the corresponding hexanal was confirmed by H-NMR.

TABLE 3

Oxidation of primary alcohols

| Entry[a] | R | R[1] | Solvent | Temp. (° C.) | Time(h) | Conversion (%)[b] |
|---|---|---|---|---|---|---|
| 1 | Ph | H | neat | 100 | 2 | >98 |
| 2[c] | H$_3$C—CH$_{2-4}$ | H | neat | 70 | 16 | 17 |
| 3[c] | Me | H | neat | 70 | 16 | 31 |
| 4[d] | H$_3$C—CH$_{2-4}$ | H | Toluene | 100 | 16 | 26 |

[a]Performed under 1 atm. O$_2$, Cu(0)-wire (10 w.t. % of Cu, the Cu(0)-wire were cut into small pieces), and TEMPO (5 mol %) at 100° C. under neat conditions.
[b]Determined by $^1$H NMR spectra on the crude reaction mixture.
[c]30 w.t. % of Cu$^{(0)}$-wire was used and TEMPO (5 mol %), at 70° C.
[d]30 w.t. % of Cu$^{(0)}$-wire was used and TEMPO (5 mol %), in toluene at 100° C., C = 0.4 M.
1 atm = about 0.1 MPa

Example 4

The Oxidation Reaction of Lignin with Only 10 wt % Cu-(0)-Plate.

The results are shown in table 4 below.

TABLE 4

| Entry[a] | Catalyst | Co-oxidant | a Wt [%][b] | b Wt [%][b] | c Wt [%][b] | d Wt [%][b] |
|---|---|---|---|---|---|---|
| 1[c] | Cu$^{(0)}$-plate-(300 mg) | — | 2.2 | 0.4 | 0.9 | — |
| 2[d] | Cu$^{(0)}$-plate-(53 mg) | — | 1.5 | 0.2 | 1.3 | — |

[a]Performed under 1 atm. or about 0.1.1325 MPa O$_2$, Organo. solv. lignin were used here. Concentration, C = 0.3 M.
[b]Calculated yields based on GC-mass.
[c]0.6 mmol, 118 mg of org. solv. lignin were used.
[d]2.4 mmol, 472 mg of org.solv. lignin were used.

Example 5

2-Oxidation of Softwood (Birch) in One-Pot:
The results are shown in table 5 below.

TABLE 5

[soft wood] → (Cu(0)-plate, 2M NaOH, O₂, 18 h, 100° C.) → a (4-hydroxy-3-methoxybenzaldehyde) + b (4'-hydroxy-3'-methoxyacetophenone) + c (4-hydroxy-3-methoxybenzoic acid) + d (2-methoxyphenol)

| Entry[a] | Catalyst | Co-oxidant | a Wt [%][b] | b Wt [%][b] | c Wt [%][b] | d Wt [%][b] |
|---|---|---|---|---|---|---|
| 1 | Cu(0)-plate-(300 mg) | — | 3.5 | 0.3 | 1.0 | — |

[a]236 mg, 1,2 mmol of soft wood were used here. Concentration, C = 0.3 M.
[b]Calculated yields based on GC-mass.

Example 6

Oxidation of Softwood in Two-Step

In step a) neat softwood (Birch) was reacted with copper under $O_2$ for 16 h and next 2M NaOH was added. The reaction was stirred at 100° C. for additional 16 h. The results are shown in table 6 below.

TABLE 6

[soft wood] → (Cu(0)-plate, O₂, 18 h, 100° C.) → (2M NaOH, 18 h, 100° C.) → a + b + c + d

| Entry[a] | Catalyst | Co-oxidant | a Wt [%][b] | b Wt [%][b] | c Wt [%][b] | d Wt [%][b] |
|---|---|---|---|---|---|---|
| 1 | Cu(0)-plate-(300 mg) | — | 2.4 | 0.3 | 1.4 | — |
| 2 | Cu(0)-plate-(300 mg) | TEMPO | 3.8 | 0.3 | 1.7 | — |

[a]236 mg, 1,2 mmol of soft wood were used here. Concentration, C = 0.3 M.
[b]Calculated yields based on GC-mass.

Example 7

Copper Catalyzed Aerobic Oxidation of Lignin

In table 7 shows selected optimizing condition reactions, whereby different co-catalysts (co-oxidants) and solvents are tested.

TABLE 7

| Entry | Catalyst | Co-oxidant | Solvent | Time [h] | Conv. [%][a] |
|---|---|---|---|---|---|
| 1 | Cu(0)-plate (400mg) | TEMPO | Neat | 18 | 32% |
| 2 | Cu(0)-plate (400mg) | — | Neat | 18 | <2% |
| 3 | Cu(0)-plate (400mg) | Hydroquinone | Neat | 18 | <2% |
| 4 | Cu(0)-plate (400mg) | Lignosulfonate | Neat | 18 | <2% |
| 5 | Cu(0)-plate (16mg) | TEMPO | NaOH 2M | 18 | 7% |
| 6 | Cu(0)-plate (16mg) | Hydroquinone | NaOH 2M | 18 | 26% |
| 7 | Cu(0)-plate (16mg) | Lignosulfonate | NaOH 2M | 18 | 20% |
| 8 | Cu(0)-plate (16mg) | — | NaOH 2M | 18 | 9% |
| 9 | — | — | NaOH 12M | 18 | <2% |
| 10 | Cu(0)-plate (400mg) | TEMPO | Neat | 18 | 32% |
| 11 | Cu(0)-plate (70mg) | TEMPO | Neat | 18 | 15% |
| 12 | Cu(0)-plate(20mg) | TEMPO | Neat | 18 | 2% |

[a]mass of the vanillin formed based on GC-Mass.
[a]mass of the vanillin formed based on GC-Mass.

Example 8

Reaction Time Screening for the Cu(0)-Plate Oxidation Reaction of the Lignin Model.

The effect of reaction time for step a) of the process was investigated. The results are shown in table 8 below.

TABLE 8

| Entry | Catalyst | Time [h] | Conversion [%][a] |
|---|---|---|---|
| 1 | Cu(0)-plate (200-250mg), 0.7 × 0.3 cm | 0.5 | 2.0 |
| 2 | Cu(0)-plate (200-250mg), 0.7 × 0.3 cm | 1.0 | 3.0 |
| 3 | Cu(0)-plate (200-250mg), 0.7 × 0.3 cm | 2.0 | 9.0 |
| 4 | Cu(0)-plate (200-250mg), 0.7 × 0.3 cm | 4.0 | 13.0 |
| 5 | Cu(0)-plate (200-250mg), 0.7 × 0.3 cm | 8.0 | 18.0 |
| 6 | Cu(0)-plate (200-250mg), 0.7 × 0.3 cm | 16.0 | 31.0 |
| 7 | Cu(0)-plate (200-250mg), 0.7 × 0.3 cm | 24.0 | 28.0 |
| 8 | Cu(0)-plate (200-250mg), 0.7 × 0.3 cm | 48.0 | 34.0 |

[a]mass of the vanillin formed based on GC-Mass.

Example 9

Aerobic Copper Oxidation of Lignin with and without TEMPO.

The effect of a co-catalyst was investigated.

Procedure with TEMPO as a Mediator.

To a round-bottomed flask (200 ml) equipped with a magnetic stir bar was charged with lignin (2 g, 1.0 equiv.), and Cu(0)-plate catalyst and TEMPO as co-catalyst (5 mol %). The round-bottomed flask was then sealed, and the atmosphere was then changed to oxygen and oxygen balloon was connected to the reaction vessel. Next, NaOH 2 M was added (20-40 ml) and the resulting mixture was allowed to stir at 80-140° C. for 6-12 h.

After that, the reaction temperature was decreased, and the reaction mixture was neutralized with 2M HCl and extracted with an organic solvent. The extracted organic phase was evaporated, and the crude mixture was filtered through short silica gel column.

The results are shown Table 9.

TABLE 9

[Lignin] $\xrightarrow[\text{16 h, 100° C.}]{\text{2M NaOH, Co-oxidant (10 mol \%), O}_2}$ vanillin structure

| Entry[a] | Catalyst | Co-oxidant | Wt [%][b] |
|---|---|---|---|
| 1 | Cu$^{(0)}$-plate -(300mg) | TEMPO | 2.9 |
| 2 | Cu$^{(0)}$-plate-(300mg) | — | 3.0 |
| 3[c] | Cu$^{(0)}$-plate-(300mg) | — | 2.3 |
| 4[d] | Cu$^{(0)}$-plate-(300mg) | — | 4.1 |

[a]Organo.solv. lignin were used here. Concentration, C = 0.3 M.
[b]Calculated yields based on GC-mass.
[c]Reaction temperature at 140° C. Concentration, C = 0.3 M.
[d]Reaction temperature at 140° C. Concentration, C = 0.085 M.

The same results were obtained with or without TEMPO.

Elevated reaction temperature did not improve the results of the oxidation reaction.

Example 10

Using Different Type of Lignin

Table 10 shows the result of the process of the invention, whereby different types of technical lignins have been used.

TABLE 10

[Lignin] $\xrightarrow[\text{16 h, 100° C.}]{\text{2M NaOH, without TEMPO, O}_2}$ vanillin structure

| Entry | Catalyst | Lignin | Wt [%][a] |
|---|---|---|---|
| 1 | Cu$^{(0)}$-plate (200mg) | organosolv. | 3.0 |
| 2 | Cu$^{(0)}$-plate (200mg) | kraft lignin | 1.1 |
| 3 | Cu$^{(0)}$-plate (200mg) | hydrolys lignin | 0.3 |
| 4 | Cu$^{(0)}$-plate (200mg) | sulphite lignin | 0.8 |
| 5 | Cu$^{(0)}$-plate (200mg) | Lignoboost lignin | 1.8 |

[a]Calculated yields based on GC-mass.

Example 11

Copper Catalyzed Oxidation of Lignin

To a round-bottomed flask (200 ml) equipped with a magnetic stir bar was charged with lignin (2 g, 1.0 equiv.), and Cu(0)-plate catalyst. The round-bottomed flask was then sealed, and the atmosphere was changed to oxygen and oxygen balloon was connected to the reaction vessel during the whole reactions time (6-12 h). Next, NaOH 2 M was added (20-40 ml) and the resulting mixture was allowed to stir at 80-140° C. for 6-12 h.

After that, the reaction temperature was decreased, and the reaction mixture was neutralized with 2M HCl and extracted with an organic solvent. The extracted organic phase was evaporated, and the crude mixture was filtered through short silica gel column. The synthesis at 100° C., 12 h, delivered 2.7 wt. % vanillin, 0.2 wt. % acetovanilone, 0.3 wt. % vanillic acid (The calculations are based on the GC-MS analysis) and were confirmed by H-NMR analysis of the isolated product.

TABLE 11

GPC analysis for starting lignin and the recovered lignin after reaction

| Entry | Mw | Mn | Mw/Mn | Mp |
|---|---|---|---|---|
| Starting lignin | | | | |
| Peak 1 | 28889 | 28079 | 1.03 | 3117 |
| Peak 2 | 4274 | 220 | 19.43 | 31472 |
| Recovered lignin | | | | |
| Peak 1 | 27610 | 26892 | 1.02 | 30397 |
| Peak 2 | 5895 | 103 | 57.2 | 5206 |

Mw is 28889, Mn is 28079, Mp is 3117

Mw is molecular weight, Mn = Molecular number weight, Mp = molecular weight of peak maxima In addition, the GPC analysis of the starting lignin and the recovered lignin showed an increase of the measured mass due to the NaOH catalyzed condensations in the synthesis step a1) and during the work up step b).

Figure 1:
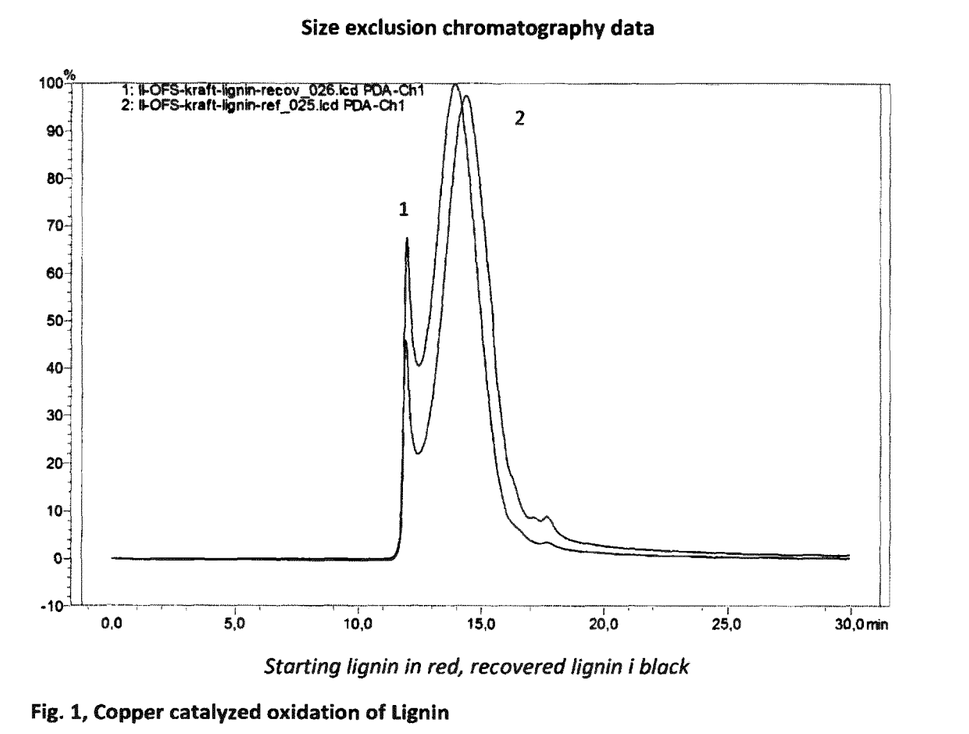
FIG. 1 shows chromatography data of copper catalyzed oxidation of lignin (Example 9)
Figure 2A:
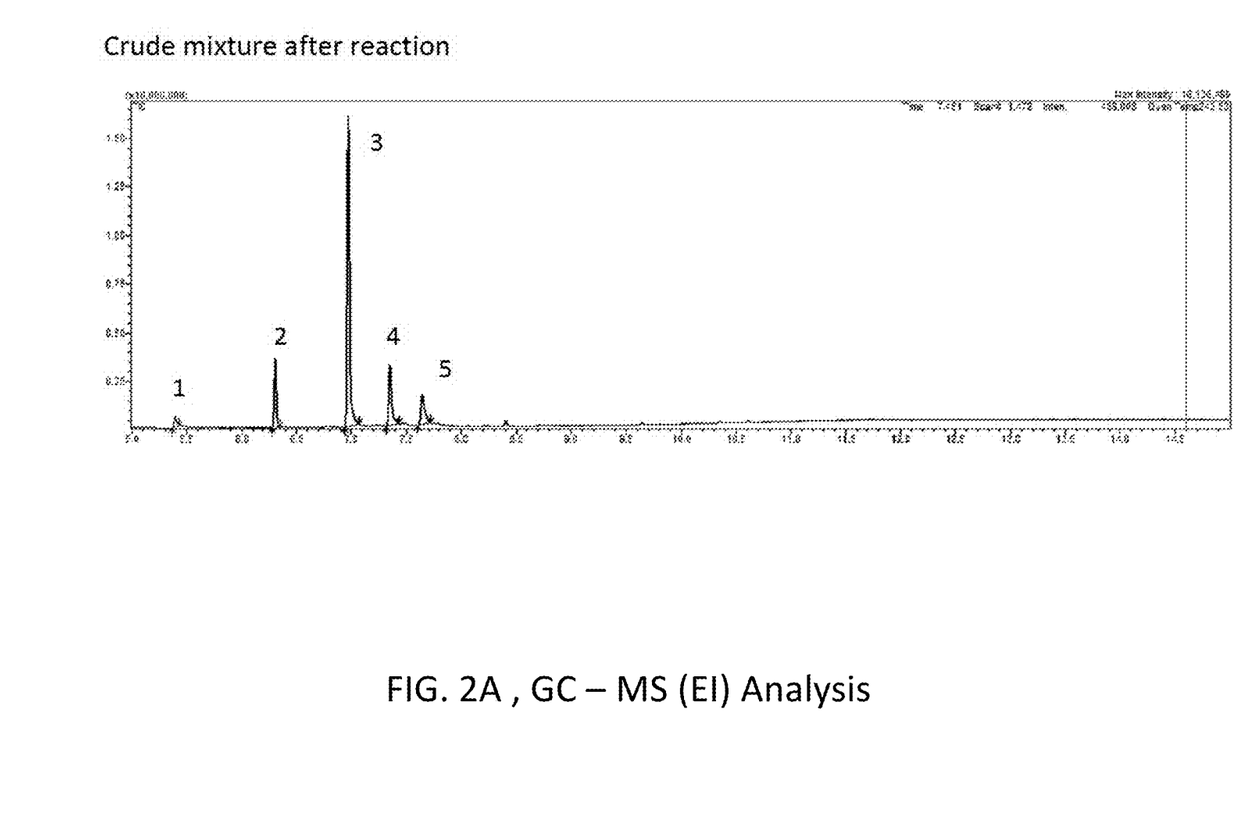
FIGS. 2A, 2B, 2C shows a GC-MS (EI) analysis (Example 9)
Figure 2B:
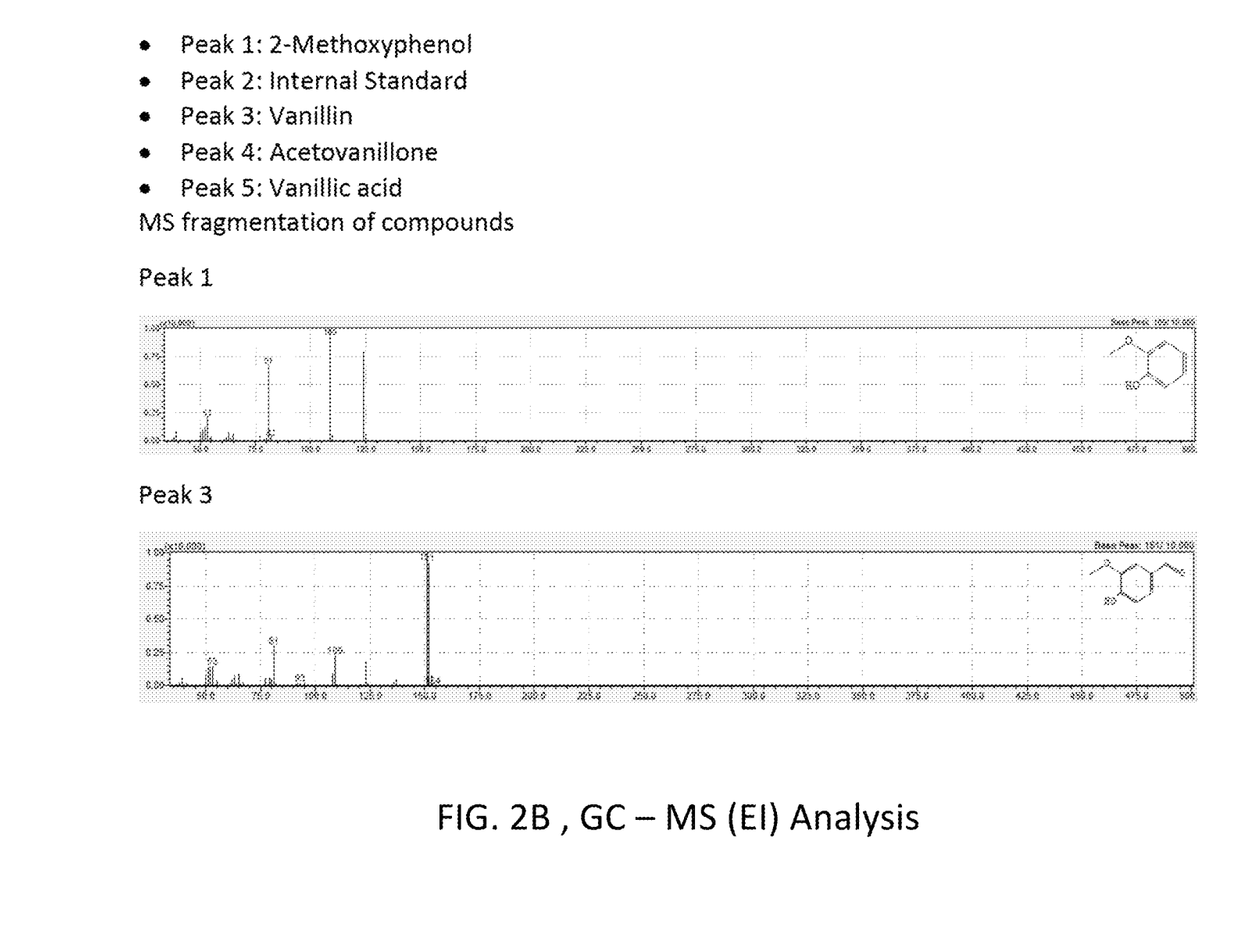
Figure 2C:
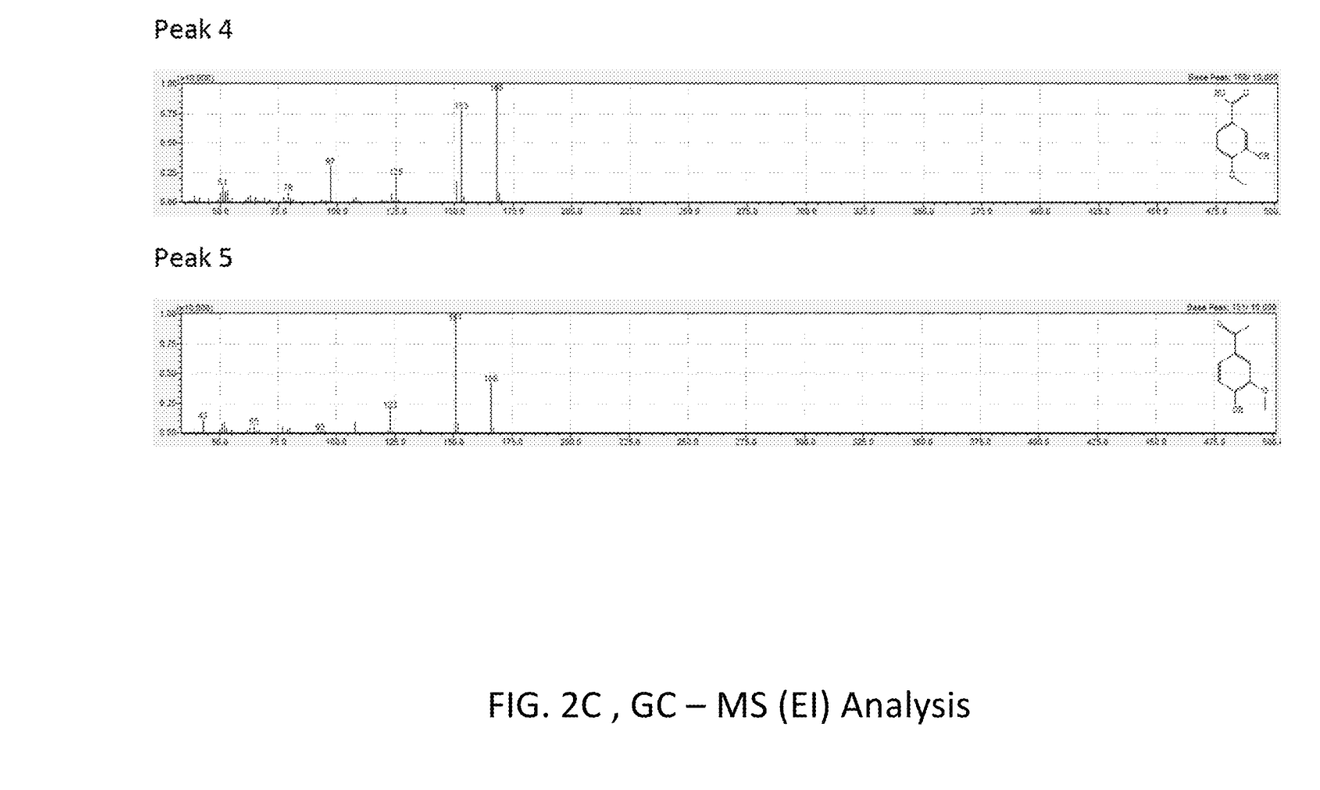

Further on, the GC-MS analysis confirmed the formation of the reported products (FIGS. 1 and 2).

Example 12a

Copper Catalyzed Oxidation of Softwood

To a round-bottomed flask (25 ml) equipped with a magnetic stir bar was charged with softwood (Birch) (1 g, 1.0 equiv.), and Cu(0)-plate catalyst. The round-bottomed flask was then sealed, and the atmosphere was then changed to oxygen and oxygen balloon was connected to the reaction vessel, during the whole reaction time (8-12 h).

Next, NaOH 2 M was added (10-30 ml) and the resulting mixture was allowed to stir at 70-100° C. for 8-12 h.

After that, the reaction temperature was decreased, and the reaction mixture was neutralized with 2M HCl and extracted with an organic solvent. The extracted organic phase was evaporated, and the crude mixture was filtered through short silica gel column. The synthesis delivered 1.0 wt. % vanillin, 0.1 wt. % acetovanilone, 0.3 wt. % vanillic acid (The calculations are based on the GC-MS analysis) and were confirmed by H-NMR analysis of the isolated product.

In addition, we were able to recycle the start material, the softwood in several cycles.

Example 12b

Metal-Free Oxidation of Softwood

A round-bottomed flask (25 ml) equipped with a magnetic stir bar was charged with softwood (Birch) (1 g, 1.0 equiv.). The round-bottomed flask was then sealed, and the atmosphere was then changed to oxygen by connecting an oxygen balloon to the reaction vessel if $O_2$ was used. Next, NaOH 2 M was added (10-30 ml) and the resulting mixture was allowed to stir at 70-100° C. for 8-12 h.

After that, the reaction temperature was decreased to room temperature. Next, the residue softwood was filtered off and the reaction mixture neutralized with 2M HCl. Then, the aqueous phase was extracted with an organic solvent. The extracted organic phase was evaporated, and the crude mixture was filtered through short silica gel column.

The synthesis delivered 2.1 wt. % vanillin, 0.35 wt. % acetovanilone, 1.7 wt. % vanillic acid. The calculations are based on the GC-MS analysis and were confirmed by H-NMR analysis of the isolated product.

Example 13

Procedure for Recycling of the Start Material:

After the neutralization step of the reaction mixture, the residue softwood (Birch) was filtered off and washed once with water. Next, the filtered material was placed in a new round-bottomed flask (25 ml) equipped with a magnetic stir bar was charged with Cu(0)-plate catalyst. The round-bottomed flask was sealed, and the atmosphere was changed to oxygen and oxygen balloon was connected to the reaction vessel, during the whole reaction time, 8-12 h. Next, the same amount of NaOH 2 M in the previous reaction was added (10-30 ml) and the resulting mixture was allowed to stir at 70-100° C. for 8-12 h. After that, the reaction temperature was decreased, and the reaction mixture was neutralized with 2M HCl. The solid material was filtered off and washed once with water and reused in the next cycle. The aqueous phase was extracted with an organic solvent. The extracted organic phase was evaporated, and the crude mixture was filtered through short silica gel column. As indicated in table 12, the same material could be recycled up to 6 cycles.

TABLE 12

The recycling of the start material, the softwood

[soft wood] $\xrightarrow[\text{2M NaOH, O}_2]{\text{Cu}^{(0)}\text{-plate}}$ vanillin
18 h, 100° C.

| Entry[a] | Wt [%][b] |
| --- | --- |
| 1 | 1.0 |
| 2 | 0.6 |
| 3 | 0.2 |
| 4 | 0.2 |
| 5 | 0.1 |
| 6 | 0.1 |
| 7 | 0.01 |

[a]The same start soft wood were recycled and used in the entries 1-7.
[b]Calculated mass of the vanillin formed based on GC-Mass.

Example 14

Recycled the Catalyst, the Cu(0)-Plate

The Cu(0)-plate were removed from the reaction mixture after the neutralization with 2M HCl. The Cu(0)-plate were washed with 2M HCl once and the black layer formed on the plate were scraped off and washed with water once before the plate was reused in the next reaction.

As indicated in table 13, the Cu-(0)-plate were reactive and efficiently catalyzed the oxidation reaction in many cycles.

TABLE 13

[soft wood] $\xrightarrow[\text{2M NaOH, O}_2]{\text{Cu}^{(0)}\text{-plate}}$ vanillin
18 h, 100° C.

| Entry[a] | Wt [%][b] |
| --- | --- |
| 1 | 1.0 |
| 2 | 0.9 |
| 3 | 0.9 |
| 4 | 0.9 |
| 5 | 0.9 |
| 6 | 1.1 |
| 7 | 0.9 |
| 8 | 1.1 |
| 9 | 1.1 |
| 10 | 1.0 |

[a]The same Cu[(0)]-plate were recycled and used in the entries 1-10.
[b]Calculated mass of the vanillin formed based on GC-Mass.

Example 15

Oxidation reaction of wood in 2M NaOH as solvent using oxygen or air under atmospheric pressure, delivered vanillin in 2.1 wt %, acetovanillone in 0.35 wt % and vanillic acid in 1.7 wt % (Table 14, entry 1).

TABLE 14

Oxidation of softwood, control experiments:

| Entry[a] | Catalyst | Co-oxidant | a Wt [%][b] | b Wt [%][b] | c Wt [%][b] | d Wt [%][b] |
|---|---|---|---|---|---|---|
| 1[c] | — | — | 2.1 | 0.35 | 1.7 | — |
| 2[d] | — | — | 1.0 | — | — | — |

[a]236 mg, 1,2 mmol of soft wood were used here. Concentration, C = 0.3 M.
[b]Calculated yields based on GC-mass.
[c]Control reaction, Performed in NaOH 2M, under 1 atm. $O_2$.
[d]Control reaction, Performed in NaOH 2M, without $O_2$.

1 atm. $O_2$=0.1 MPa is use of oxygen gas under atmospheric pressure.

without $O_2$=use of air under atmospheric pressure.

The reaction under normal atmosphere (air) delivered vanillin in 1 wt % as the only product (Table 14, entry 2).

The present invention is not limited to the embodiments disclosed but may be varied and modified within the scope of the following claims.

The invention claimed is:

1. A process for the production of vanillin, vanillic acid, acetovanilone, syringaldehyde, and veratraldehyde from softwood, hardwood, lignin, or a mixture thereof, comprising the step a) reacting chips of the one or more wood products in a basic solution, wherein the basic solution is an aqueous solution with bases selected from the group comprising NaOH, KOH, Ca(OH)$_2$ and Mg(OH)$_2$, at a pH between 8 and 14, wherein the basic solution has a molarity of 3 to 5 M, under an oxygen atmosphere using substantially pure oxygen, at a pressure between 0.5 and 10 MPa and wherein the temperature is below 160° C., under stirring for between 6 and 36 hours, wherein a use of a metal catalyst is disclaimed, and wherein the reaction results in one or more of vanillin, vanillic acid, acetovanilone, syringaldehyde, and veratraldehyde.

2. The process according to claim 1, wherein the pressure is between 0.5 and 1.5 MPa.

3. The process according to claim 1, wherein the temperature is between 50 and 160° C.

4. The process according to claim 1, wherein the temperature is between 70 and 140° C.

5. The process according to claim 1, wherein the pH is between 10 and 14.

6. The process according to claim 1, wherein the chips of the one or more wood products are unprepared and non-hydrolysed chips.

7. The process according to claim 1, wherein the one or more wood products are one or more short-rotation energy crops selected from softwoods and hardwoods.

8. The process according to claim 1, wherein the one or more wood products are one or more softwoods selected from the group comprising pine, spruce and cedar.

9. The process according to claim 1, wherein the one or more wood products are one or more hardwoods selected from the group comprising aspen, birch, cotton woods, beech, poplar, willow and eucalyptus.

10. The process according to claim 1, wherein the one or more wood products are lignin.

11. The process according to claim 1, wherein the process comprises a further step b) comprising neutralizing the oxidized product of step a) extracting the product with an organic phase and filtering the oxidized product.

12. The process according to claim 11, wherein the oxidized product obtained after filtering is reused in the process.

* * * * *